United States Patent
Li et al.

(10) Patent No.: US 10,634,752 B2
(45) Date of Patent: Apr. 28, 2020

(54) MOTION CORRECTED SIMULTANEOUSLY ACQUIRED MULTIPLE CONTRAST CORONARY MRI SYSTEMS AND METHODS

(71) Applicant: CEDARS-SINAI MEDICAL CENTER, Los Angeles, CA (US)

(72) Inventors: Debiao Li, So. Pasadena, CA (US); Yibin Xie, Los Angeles, CA (US); Jianing Pang, Los Angeles, CA (US); Qi Yang, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 704 days.

(21) Appl. No.: 14/853,091

(22) Filed: Sep. 14, 2015

(65) Prior Publication Data
US 2017/0074959 A1    Mar. 16, 2017

(51) Int. Cl.
*G01R 33/56* (2006.01)
*G01R 33/563* (2006.01)
*A61B 5/055* (2006.01)
*G01R 33/561* (2006.01)
*G01R 33/567* (2006.01)
(Continued)

(52) U.S. Cl.
CPC ...... *G01R 33/5635* (2013.01); *A61B 5/02007* (2013.01); *A61B 5/055* (2013.01); *A61B 5/7289* (2013.01); *G01R 33/5607* (2013.01); *G01R 33/5611* (2013.01); *G01R 33/5676* (2013.01); *G01R 33/56509* (2013.01); *G01R 33/4826* (2013.01); *G01R 33/5601* (2013.01); *G01R 33/5602* (2013.01); *G01R 33/5673* (2013.01)

(58) Field of Classification Search
CPC ... A61B 5/055; A61B 5/02007; A61B 5/7207; A61B 5/7289; G01R 33/5611; G01R 33/5635; G01R 33/4826; G01R 33/483; G01R 33/5601; G01R 33/5602; G01R 33/5607; G01R 33/5613
See application file for complete search history.

(56) References Cited

U.S. PATENT DOCUMENTS

| | | | |
|---|---|---|---|
| 2005/0043614 A1* | 2/2005 | Huizenga | A61B 5/055 600/427 |
| 2010/0134103 A1* | 6/2010 | Edelman | G01R 33/5635 324/309 |

(Continued)

OTHER PUBLICATIONS

Fan et al., "Multi-contrast atherosclerosis characterization of carotid plaque with a single 5-min scan: technical development and clinical feasibility". Journal of Cardiovascular Magnetic Resonance 2014, 16:53 pp. 1-12.*

(Continued)

*Primary Examiner* — Katherine L Fernandez
*Assistant Examiner* — Yi-Shan Yang
(74) *Attorney, Agent, or Firm* — Nixon Peabody LLP (57) ABSTRACT

In various embodiments, the present application discloses systems and methods for magnetic resonance imaging (MRI) of coronary arteries. In various embodiments, the invention allows for motion corrected, simultaneously acquired multiple contrast weighted images with whole-heart coverage and isotropic high resolution. In some embodiments, the invention teaches using interleaved preparatory pulses, a 3D radial golden angle trajectory and 100% respiratory gating efficiency.

15 Claims, 9 Drawing Sheets
(6 of 9 Drawing Sheet(s) Filed in Color)

(51) Int. Cl.
G01R 33/565 (2006.01)
A61B 5/00 (2006.01)
A61B 5/02 (2006.01)
G01R 33/48 (2006.01)

(56) References Cited

U.S. PATENT DOCUMENTS

| | | | | |
|---|---|---|---|---|
| 2011/0181283 | A1* | 7/2011 | Grinstead | G01R 33/5602 324/309 |
| 2011/0295579 | A1* | 12/2011 | Tang | A61B 6/466 703/9 |
| 2014/0180132 | A1* | 6/2014 | Shan | A61B 5/0059 600/476 |
| 2015/0323636 | A1* | 11/2015 | Wang | G01R 33/5607 600/419 |
| 2017/0061620 | A1* | 3/2017 | Park | G06T 5/001 |

OTHER PUBLICATIONS

Hernandez et al., "Color fusion of magnetic resonance images improves intracranial volume measurement in studies of aging". Open Journal of Radiology, 2012, 1, 1-9.*
Shanghai Chenguang Medical Technologies Co., LTD, company profile, 2010. This reference discloses various RF coils developed in the company for MR imaging applications.*
Pang et al., "Whole-heart coronary MRA with 100% respiratory gating efficiency: self-navigated three-dimensional retrospective image-based motion correction (TRIM)". Published in MRM, Jan. 2014; 71(1), pp. 1-18. (Year: 2014).*
Jun. et al., "Self-calibrated multiple-echo acquisition with radial trajectories using the conjugate gradient method". Published online JMRI 2011, 33(4): 980-987. (Year: 2014).*
Ma et al., "Myocardial Perfusion Magnetic Resonance Imaging Using Sliding-Window Conjugate-Gradient Highly Constrained Back-Projection Reconstruction for Detection of Coronary Artery Disease" Am J Cardiol 2012; 109:1137-1141. (Year: 2012).*
Pang et al., "Accelerated whole-heart coronary MRA using motion-corrected sensitivity encoding with three-dimensional projection reconstruction". Published online Jan. 16, 2014, pp. 284-291. (Year: 2014).*
Avants, B.B. et al., "Symmetric diffeomorphic image registration with cross-correlation: Evaluating automated labeling of elderly and neurodegenerative brain," ScienceDirect, Medical Image Anayisis 12 (2008) 26-41 (16 pages).
Balu, N. et al., "Cartoid Plaque Assessment Using Fast 3D Isotropic Resolution Black-Blood MRI," Magnetic Resonance in Medicine 65:627-637 (2011) (11 pages).
Batchelor, P.G. et al., "Matrix Description of General Motion Correction Applied to Multishot Images," Magnetic Resonance in Medicine 54:1273-1280 (2005) (8 pages).
Boussel, L. et al., "Altherosclertic Plaque Progression in Cartoid Arteries: Monitoring with High-Spatial-Resolution MR Imaging—Multicenter Trial," Radiology: vol. 252: No. 3—Sep. 2009, radiology.rsnajnls.org (8 pages).
Chan, R. et al., "Temporal Stability of Adaptive 3D Radial MRI Using Multidimensional Golden Means," Magnetic Resonance in Medicine 61:354-363 (2009) (10 pages).
Chandarana, H. et al., "Free-Breathing Radial 3D Fat-Suppressed T1-Weighted Gradient Echo Sequence," A Viable Alternative for Contrast-Enhanced Liver Imaging in Patients Unable to Suspend Respiration, Investigative Radiology, vol. 46, No. 10, Oct. 2011 (6 pages).
Chung, Y. et al., "2137 T1-weighted 3D dark blood TSE for carotid artery disease imaging—preliminary experience," Journal of Cardiovascular Magnetic Resonance, Oct. 22, 2008, 10(Suppl I):A406 (3 pages).
Coppo, S. et al., "Free-Running 4D Whole-Heart Self-Navigated Golden Angle MRI: Initial Results," Magnetic Resonance in Medicine 74:1306-1316 (2015) (11 pages).

Crowe, L. et al., "Votume-Selective 3D Turbo Spin Echo Imaging for Vascular Wall Imaging and Distensibility Measurement," Journal of Magnetic Resonance Imaging 17:572-580 (2003) (9 pages).
Deng, Z. et al., "Four-dimensional MRI Using Three-Dimensional Radial Sampling with Respiratory Self-Gating to Characterize Temporal Phase-Resolved Respiratory Motion in the Abdomen," Magnetic Resonance in Medicine, May 2015 (13 pages).
Fan, Z., et al., "3D Noncontrast MR Angiography of the Distal Lower Extremities Using Flow-Sensitive Dephasing (FSD)—Prepared Balanced SSFP," Magnetic Resonance in Medicine 62:1523-1532 (2009) (10 pages).
Fan, Z. et al., "Carotid Arterial Wall MRI at 3T Using 3D Variable-Flip-Angle Turbo Spin-Echo (TSE) with Flow-Sensitive Dephasing (FSD)," Journal of Magnetic Resonance Imaging 31:645-654 (2010) (10 pages).
Hardy, C. et al., "Coronary Angiography by Real-Time MRI With Adaptive Averaging," Magnetic Resonance in Medicine 44:940-946 (2000) (7 pages).
Huang, T. et al., "Automatic calibration of trigger delay time for cardiac MRI," NMR in Biomedicine, Published online in Wiley Online Library: Jan. 29, 2014 (8 pages).
Jahnke, C. et al., "A new approach for rapid assessment of the cardiac rest period for coronary MRA," Journal of Cardiovascular Magnetic Resonance (2005) 7, 395-399 (5 pages).
Kelly, J. et al., "Magnetic resonance direct thrombus imaging: a novel technique for imaging venous thromboemboli," Thromb Haemost 2003; 89: 773-82 (10 pages).
Kim, D. et al., "Accelerated Phase-Contrast Cine MRI Using k-t Sparse-Sense," Magnetic Resonance in Medicine 67:1054-1064 (2012) (11 pages).
Koktzoglou, I. et al., "Diffusion-Prepared Segmented Steady-State Free Precession: Application to 3D Black-Blood Cardiovascular Magnetic Resonance of the Thoracic Aorta and Carotid Artery Walls," Journal of Cardiovascular Magnetic Resonance (2007) 9, 33-42 (10 pages).
Leach, J. et al., "Imaging of Cerebral Venous Thrombosis: Current Techniques, Spectrum of Findings, and Diagnostic Pitfalls," Clinical Applications of Vascular imaging, RadoGraphics 2006; 26:S19-S43 (24 pages).
Li, L. et al., "DANTE-Prepared Pulse Trains: A Novel Approach to Motion-Sensitized and Motion-Suppressed Quantitative Magnetic Resonance Imaging," Magnetic Resonance in Medicine 68:1423-1438 (2012) (16 pages).
Li, D. et al., "Coronary Arteries: Magnetization-prepared Contrast-enhanced Three-dimensional Volume-targeted Breath-hold MR Angiography," Radiology 2001; 219:270-277 (8 pages).
Lingala, S. et al., "Deformation corrected compressed sensing (DC-CS): a novel framework for accelerated dynamic MRI," arXiv:1405.7718v2 [cs.CV] Sep. 2, 2014 (14 pages).
Mihai, G. et al., "T1-Weighted-Space Dark Blood Whole Body Magnetic Resonance Angiography (DB-WBMRA): Initial Experience," Journal of Magnetic Resonance Imaging 31:502-509 (2010) (8 pages).
Mugler, J. III, "Optimized Three-Dimensional Fast-Spin-Echo MRI," Journal of Magnetic Resonance Imaging 39:745-767 (2014) (23 pages).
Pang, J. et al., "Whole-Heart Coronary MRA with 100% Respiratory Gating Efficiency: Self-Navigated Three-Dimensional Retrospective Image-Based Motion Correction (TRIM)," Magnetic Resonance in Medicine 71:67-74 (2014) (8 pages).
Pang, J. et al., "ECG and Navigator-Free Four-Dimensional Whole-Heart Coronary MRA for simultaneous Visualization of Cardiac Anatomy and Function," Magnetic Resonance in Medicine 72:1208-1217 (2014) (10 pages).
Park, J. et al., "Optimized T1-Weighted Contrast for Single-Slab 3D Turbo Spin-Echo Imaging With Long Echo Trains: Application to Whole-Brain Imaging," Magnetic Resonance in Medicine 58:982-992 (2007) (11 pages).
Piccini, D. et al., "Is There an Optimal Respiratory Reference Position for Sell-Navigated Whole-Heart Coronary MR Angiography?," 2015 Wiley Periodicals, Inc. (8 pages).

(56) References Cited

OTHER PUBLICATIONS

Qiao, Y. et al., "Intracranial Arterial Wall Imaging Using Three-Dimensional High Isotropic Resolution Black Blood MRI at 3.0 Tesla," Journal of Magnetic Resonance Imaging 34:22-30 (2011) (9 pages).

Rasche, V. et al., "Automatic extraction of the low-motion phases of the heart," Proc. Intl. Soc. Mag. Reson. Med. 15 (2007) (1 page).

Royuela-Del-Val, J. et al., "Nonrigid Groupwise Registration for Motion Estimation and Compensation in Compressed Sensing Reconstruction of Breath-Hold Cardiac Cine MRI," Magnetic Resonance in Medicine 75:1525-1536 (2016) (12 pages).

Saam, T. et al., "Carotid Plaque Composition Differs Between Ethno-Racial Groups," An MRI Pilot Study Comparing Mainland Chinese and American Caucasian Patients, Arterioscler Thromb Vasc. Biol. Mar. 2005 (6 pages).

Saposnik, G. et al., "Diagnosis and Management of Cerebral Venous Thrombosis," A Statement for Healthcare Professionals From the American Heart Association/American Stroke Association, Stroke 2011;42:1158-1192 (35 pages).

Schmidt, J. et al., "Nonrigid Retrospective Respiratory Motion Correction in Whole-Heart Coronary MRA," Magnetic Resonance in Medicine 66;1541-1549 (2011) (9 pages).

Song, H. et al., "Multislice Double Inversion Pulse Sequence for Efficient Black-Blood MRI," Magnetic Resonance in Medicine 47:616-620 (2002) (5 pages).

Stehning, C. et al., "Fast Isotropic Volumetric Coronary MR Angiography Using Free-Breathing 3D Radial Balanced FFE Acquisition," Magnetic Resonance in Medicine 52:197-203 (2004) (7 pages).

Stehning, C. et al., "Free Breathing 3D Balanced FFE Coronary Magnetic Resonance Angiography with Prolonged Cardiac Acquisition Windows and Intra-RR Motion Correction," Magnetic Resonance in Medicine 53:719-723 (2005) (5 pages).

Takano, K. et al., "Characterization of carotoid atherosclerosis with black-blood carotid plaque imaging using variable flip-angle 3D turbo spin-echo: Comparison with 2D turbo spin-echo sequences." European Journal of Radiology 81 (2012) e304-e309 (6 pages).

Takano, K. et al., "MRI of intracranial vertebral artery dissection: evaluation of intramural haematoma using a black blood, variable-flip-angle 3D turbo spin-echo sequence," Neuroradiology (2013) 55:845-851 (8 pages).

Tustison, N. et al., "Explicit B-spline regularization in diffeomorphic image registration," Frontiers in Neuroinformatics, Methods Article, Dec. 23, 2013, vol. 7. Article 39 (13 pages).

Underhill, H. et al., "MRI of carotid atherosclerosis: clinical implications and future directions," Molecular Imaging, Nature Reviews, Cardiology, vol. 7, Mar. 2010 (9 pages).

Usman, M. et al., "Motion Corrected Compressed Sensing for Free-Breathing Dynamic Cardiac MRI," Magnetic Resonance in Medicine 70:504-516 (2013) (13 pages).

Ustun, A. et al., "Automated Identification of Minimal Myocardial Motion for Improved Image Quality on MR Angiography at 3 T," Cardiac Imaging, Technical Innovation, AJR: 188, Mar. 2007 (8 pages).

Winter, P. et al., "Improved Molecular Imaging Contrast Agent for Detection of Human Thrombus," Magnetic Resonance in Medicine 50:411-416 (2003) (6 pages).

\* cited by examiner

MOTION CORRECTED SIMULTANEOUSLY ACQUIRED MULTIPLE CONTRAST CORONARY MRI SYSTEMS AND METHODS

FIELD OF THE INVENTION

The present invention generally relates to imaging methods and systems.

BACKGROUND

The following description includes information that may be useful in understanding the present invention. It is not an admission that any of the information provided herein is prior art or relevant to the presently claimed invention.

Coronary artery disease (CAD) is the most common type of heart disease. It is the leading cause of death in the United States in both men and women. Plaque rupture is the most common type of coronary plaque complication, accounting for about 70% of fatal acute myocardial infarctions and/or sudden coronary deaths. T1-weighted (T1w) magnetic resonance imaging (MRI) with or without contrast enhancement (CE) has been used for characterizing coronary plaques, and shows promising prognostic capability for coronary events. However, the drawbacks of current protocols using conventional Cartesian acquisition and respiratory gating are a major hinderance against wide clinical application of this technique. Important drawbacks include: (a) anatomical coverage is limited to proximal coronary segments; (b) non-isotropic spatial resolution, specifically poor resolution along the base-to-apex direction; (c) a separate bright-blood MRA acquisition is needed as anatomical reference due to highly suppressed background tissue in T1w images. (d) long and unpredictable total scan time leading to patient discomfort and motion artifacts.

There is clearly a need in the art for improved imaging systems and methods.

SUMMARY OF THE INVENTION

In various embodiments, the invention teaches a method for performing magnetic resonance imaging (MRI), including: (a) positioning an object in a magnetic field; (b) using a radio frequency (RF) coil to apply one or more preparatory pulses during each of one or more repetition periods, wherein one or more of said preparatory pulses selectively suppresses the signal of one or more components of the object, based on different relaxation times of two or more components of the object; (c) applying readout pulses to the object; (d) acquiring imaging data in an interleaved fashion for different sets of images of the object during repetitions, wherein each set of images has a different contrast weighting; and (e) overlaying and color-coding images with different contrast weightings. In some embodiments, one or more preparatory pulses include a 180° inversion pulse, a T2 preparation pulse, or both a 180° inversion pulse and a T2 preparation pulse. In some embodiments, different relaxation times include spin-lattice (T1) relaxation times and/or spin-spin (T2) relaxation times. In certain embodiments, the object includes one or more portion of a subject's heart. In some embodiments, the object includes a subject's heart.

In various embodiments, the invention teaches a method for compensating for motion-induced artifacts in magnetic resonance imaging (MRI) data including multiple image contrasts, said method includes the steps of: (a) separating MRI data into a plurality of datasets based on different image contrasts; (b) sorting each dataset into different data groups corresponding to different motion phases using a diaphragm navigator or a self-navigation signal as a uniform reference; (c) selecting the dataset with the highest signal-to-noise ratio for motion estimation; (d) estimating the motion between a reference data group and the rest of the data groups using image-based 3D affine registration; and (e) modifying each dataset and adjusting trajectory based on translation vectors and affine transform matrices to compensate for the estimated motion, thereby resulting in motion-corrected k-space data and trajectory. In some embodiments, the motion-corrected k-space data and trajectory are incorporated into a conjugate gradient (CG-) sensitivity encoding (SENSE) reconstruction framework including coil sensitivity self-calibration. In some embodiments, the coil sensitivity self-calibration includes: (a) reconstructing motion-corrected individual coil images by gridding; (b) calculating coil sensitivity maps by using the eigenvector of local signal covariance matrices as the estimate of the respective sensitivity values at a specific spatial location; and (c) averaging the local image covariance matrices to suppress streaking artifacts. In certain embodiments, the averaging operation is implemented in MATLAB using a graphical processing unit (GPU). In some embodiments, the sensitivity encoding operation is performed using a gridding/regridding approach with a density compensation function (DCF) iteratively calculated from the k-space trajectory to compensate for sampling nonuniformity. In certain embodiments, the method further includes accelerating convergence of CG iterations through preconditioning by density compensation.

In various embodiments, the invention teaches a method that includes: (a) acquiring magnetic resonance (MR) data resulting from a plurality of repetition times (TRs), and (b) adjusting an inversion time retrospectively after data acquisition for selecting the best available image contrast weighting for distinguishing lesions from normal tissue. In some embodiments, MR data are acquired using 3D radial trajectory with a golden angle. In some embodiments, the acquired MR data during each TR are segmented into a plurality of groups, each with a distinct inversion time. In some embodiments, the method further includes applying a sliding window filter to combine segmented MR data with different inversion times, while preserving distinct contrast weightings, thereby obtaining segmented and filtered MR data. In certain embodiments, the segmented and filtered MR data are reconstructed into multi-frame images. In certain embodiments, a density compensation function for each phase is calculated from corresponding filtered k-space data. In some embodiments, the method further includes displaying and selecting a frame with the best available contrast weighting.

In various embodiments, the invention teaches a non-transitory machine-readable medium having machine executable instructions for causing one or more processors of a magnetic resonance imaging (MRI) machine to execute a method that includes: (a) using a radio frequency (RF) coil to apply none, one, or more preparatory pulses during each of one or more repetition period to selectively suppress the signal of one or more components of an object, based on different relaxation times of the one or more components; (b) applying readout pulses to the object; (c) acquiring imaging data in an interleaved fashion for different sets of images during repetitions; and (d) overlaying and color-coding images with different contrast weightings. In some embodiments, one or more preparatory pulses include a 180° inversion pulse, a T2 preparation pulse, or both. In certain embodiments, different relaxation times include spin-lattice (T1) relaxation times and/or spin-spin (T2) relaxation times.

In certain embodiments, the MRI machine is a 3.0T machine. In certain embodiments, the object includes one or more portion of a subject's heart. In some embodiments, the object includes a subject's heart.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments are illustrated in the referenced figures. It is intended that the embodiments and figures disclosed herein are to be considered illustrative rather than restrictive.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Westbrook et al., *MRI in Practice* 4$^{th}$ ed., and Guyton and Hall, *Textbook of Medical Physiology* 12$^{th}$ ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

"Conditions," "disease conditions," and "cardiovascular conditions," as used herein, may include but are in no way limited to coronary artery disease (CAD), as well as other conditions associated with abnormalities of the heart. As used herein, the term "CAD" may include, but is in no way limited to inflammation in an artery, plaque in an artery, plaque rupture, an unstable plaque, a damaged arterial wall, intra-plaque hemorrhage, necrotic lipid core, and the like.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

"ECG," as used herein, refers to electrocardiogram.

"FLASH MRI," as used herein, refers to fast low angle shot magnetic resonance imaging, which is synonymous with spoiled gradient echo (SPGR) magnetic resonance imaging.

"CE," as used herein, refers to contrast enhancement.

In some embodiments, the invention teaches systems and methods for characterizing arterial plaque. The significant advantages of systems and methods described herein include, but are in no way limited to (1) whole-heart coverage, (2) isotropic high spatial resolution; and (3) simultaneously acquired bright-blood images for luminal assessment and anatomical reference.

In various embodiments, the MRI data is acquired using a 3D golden angle radial acquisition scheme without breath holding. By employing an interleaved acquisition scheme, images with multiple contrast weightings (i.e. dark-blood and bright-blood) are acquired with one scan. Respiratory motion is compensated with a joint motion correction scheme for all image contrast weightings with 100% gating efficiency, and therefore the total scan time is significantly reduced. A brief summary of exemplary pulse sequences and image reconstruction schemes are provided below, followed by additional exemplary applications of each technology in the context of various inventive systems and methods.

Pulse Sequences

Figure 1:
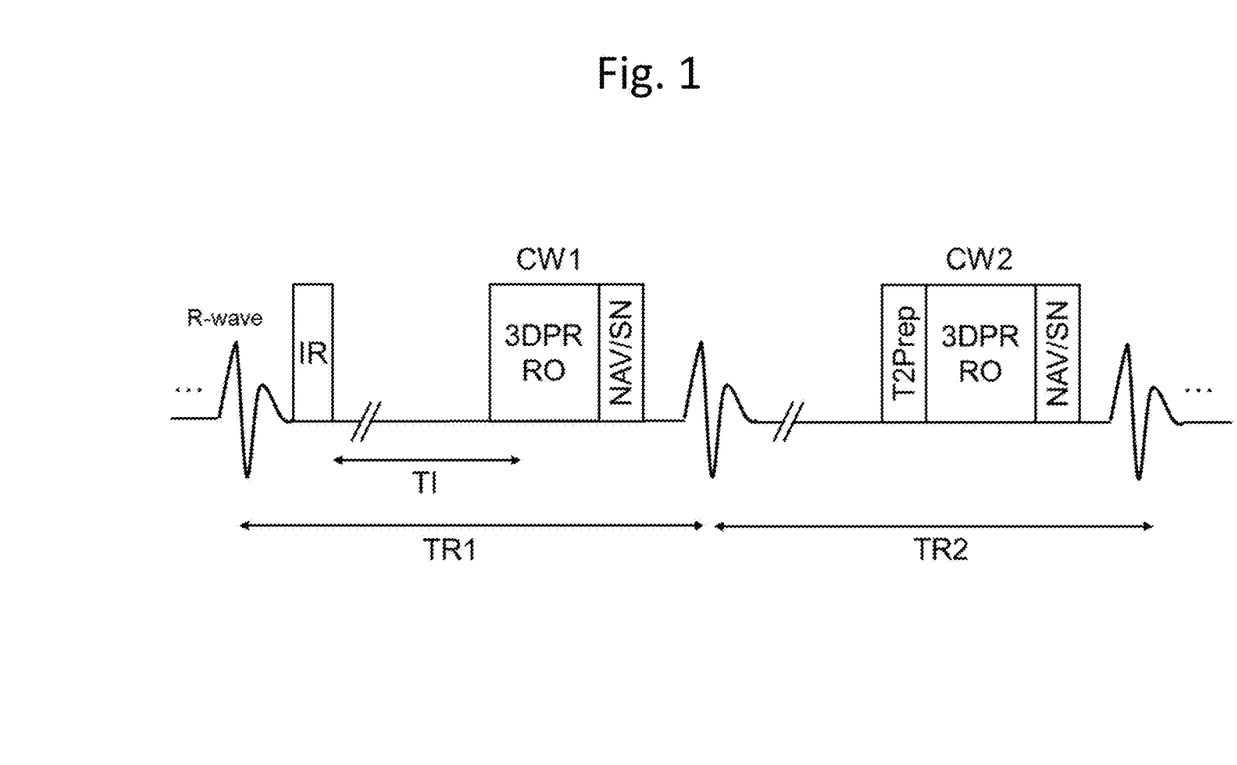
FIG. 1 depicts, in accordance with an embodiment of the invention, a schematic of an MRI pulse sequence chart illustrating the interleaved acquisition of images with different contrast weightings using preparatory pre-pulses.
Figure 2:
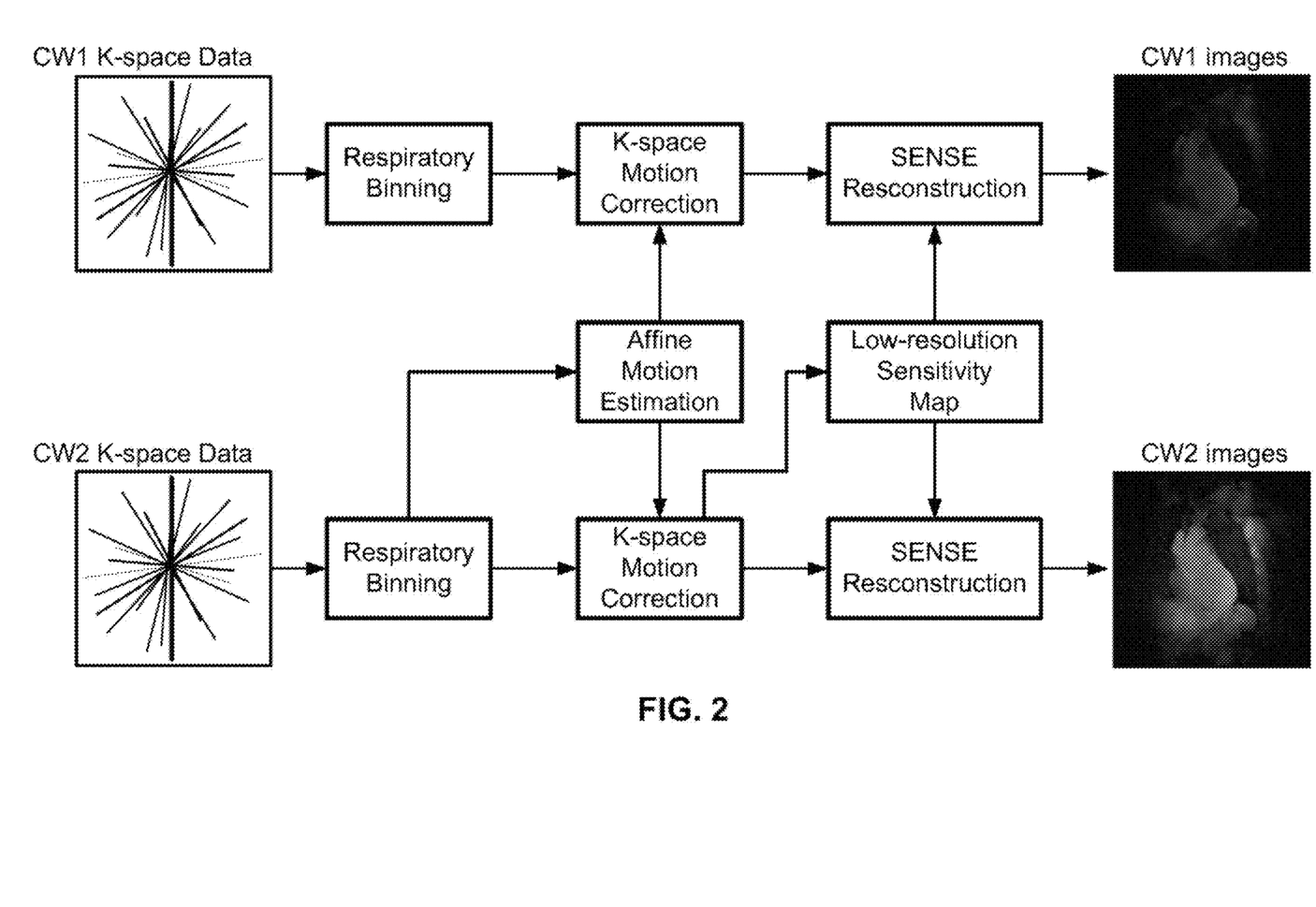
FIG. 2 depicts, in accordance with an embodiment of the invention, a schematic flow chart of the processes of compensating for motion-induced artifacts in magnetic resonance (MR) measurement data with multiple image contrasts.
Figure 3A:
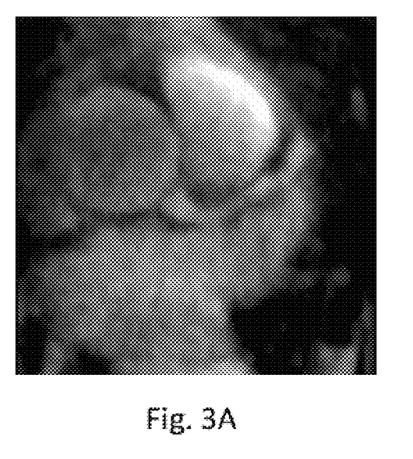
FIG. 3A depicts, in accordance with an embodiment of the invention, an in-plane image of coronary arteries with bright-blood contrast weight.
Figure 3B:
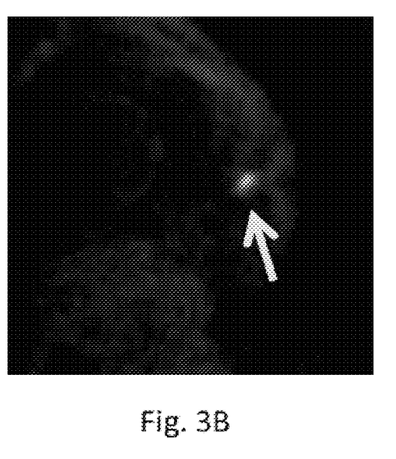
FIG. 3B depicts, in accordance with an embodiment of the invention, an in-plane image of coronary arteries with dark-blood contrast weighting with an arrow pointing to an anomaly.
Figure 3C:
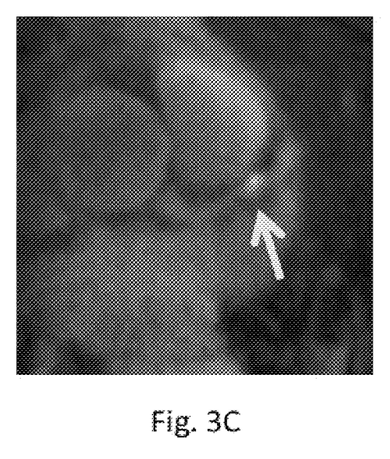
FIG. 3C depicts, in accordance with an embodiment of the invention, an in-plane image of coronary arteries with a fusion of bright-blood and dark-blood contrast weighting with an arrow pointing to the anomaly.
Figure 3D:
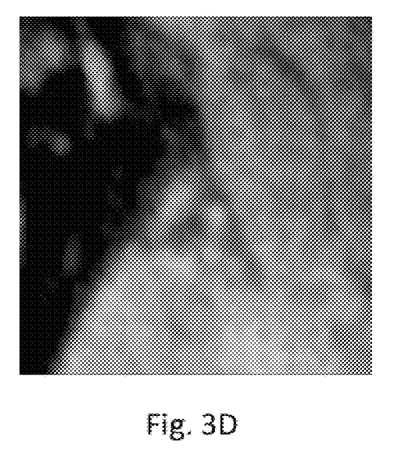
FIG. 3D depicts, in accordance with an embodiment of the invention, a cross-sectional image of coronary arteries with bright-blood contrast weighting.
Figure 3E:
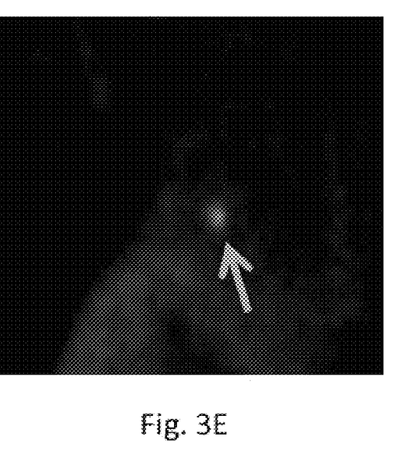
FIG. 3E depicts, in accordance with an embodiment of the invention, a cross-sectional image of coronary arteries with dark-blood contrast weighting with an arrow pointing to the anomaly.
Figure 3F:
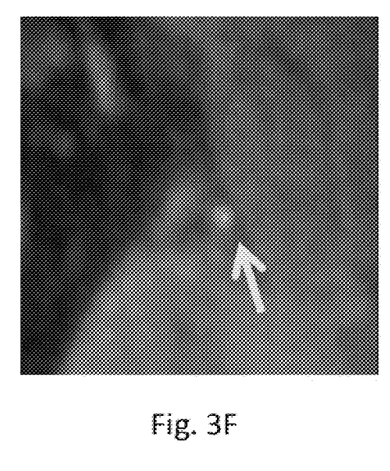
FIG. 3F depicts, in accordance with an embodiment of the invention, a cross-sectional image of coronary arteries with a fusion of bright-blood and dark-blood contrast weighting with an arrow pointing to the anomaly.
Figure 4A:
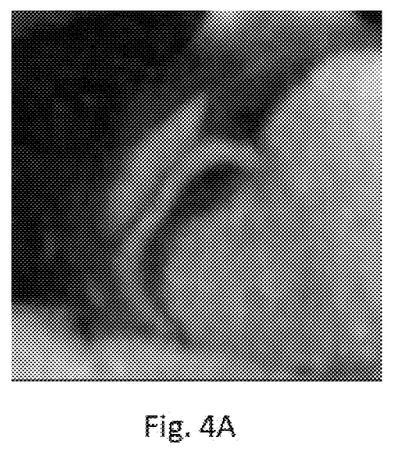
FIG. 4A depicts, in accordance with an embodiment of the invention, an image of coronary arteries with bright-blood contrast weighting before a gadolinium contrast agent injection.
Figure 4B:
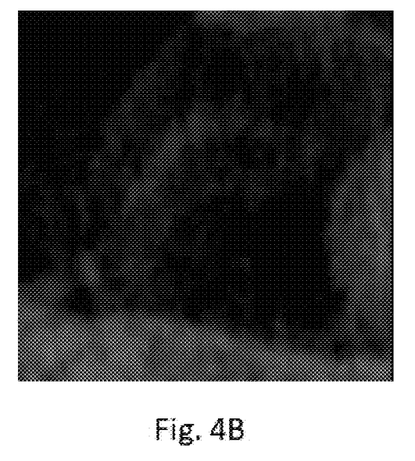
FIG. 4B depicts, in accordance with an embodiment of the invention, an image of coronary arteries with dark-blood contrast weighting before a gadolinium contrast agent injection.
Figure 4C:
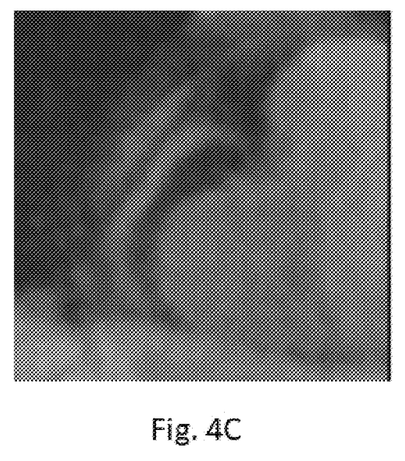
FIG. 4C depicts, in accordance with an embodiment of the invention, an image of coronary arteries with a fusion of bright-blood and dark-blood contrast weighting before a gadolinium contrast agent injection.
Figure 4D:
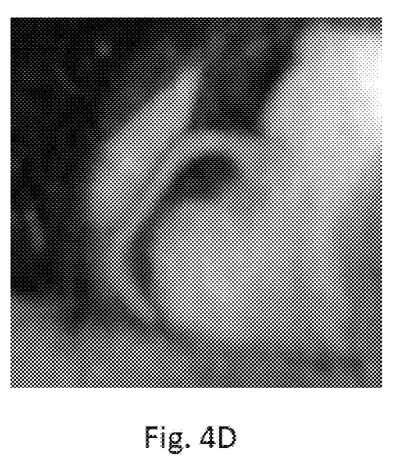
FIG. 4D depicts, in accordance with an embodiment of the invention, an image of coronary arteries with bright-blood contrast weighting after a gadolinium contrast agent injection.
Figure 4E:
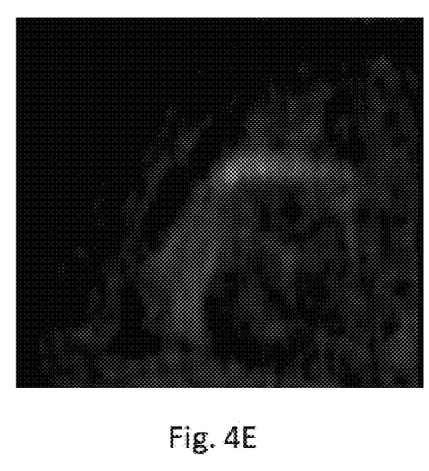
FIG. 4E depicts, in accordance with an embodiment of the invention, an image of coronary arteries with dark-blood contrast weighting after a gadolinium contrast agent injection.
Figure 4F:
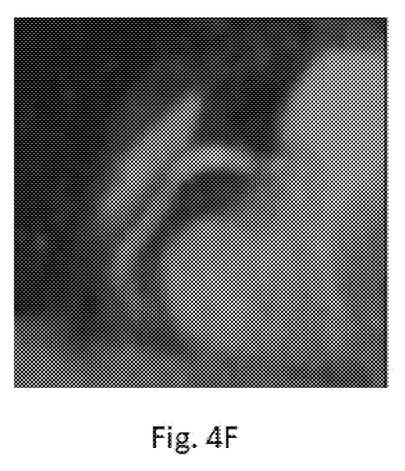
FIG. 4F depicts, in accordance with an embodiment of the invention, an image of coronary arteries with a fusion of bright-blood and dark-blood contrast weighting after a gadolinium contrast agent injection.
Figure 5:
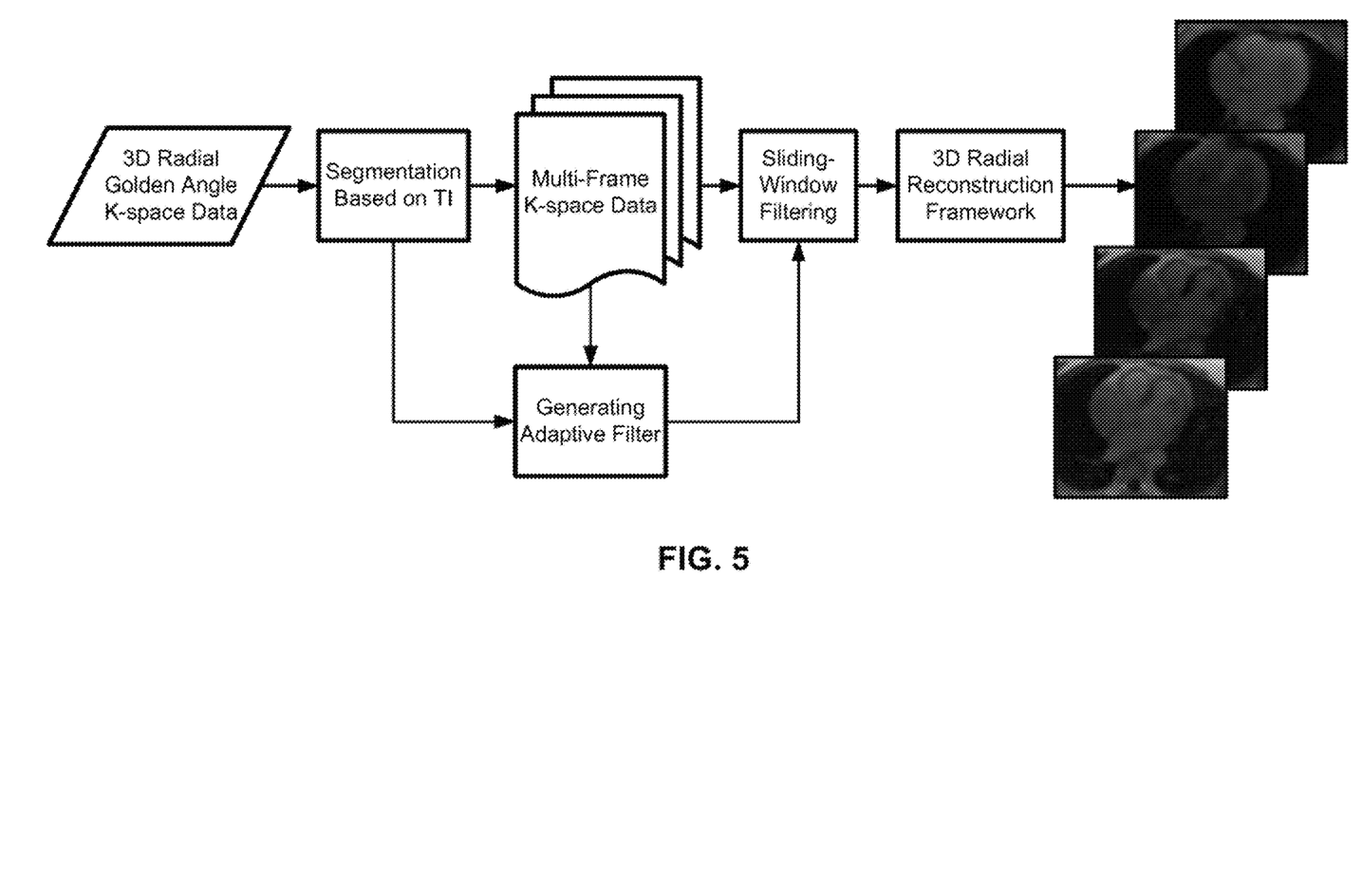
FIG. 5 depicts, in accordance with an embodiment of the invention, a schematic flow chart of the processes of adjusting inversion time after data acquisition for selecting the optimal image contrast weighting.

In various embodiments, the pulse sequence of the systems and methods described herein comprises, consists of, or consists essentially of an ECG-gated, inversion recovery (IR) prepared spoiled gradient echo (FLASH) acquisition with golden-angle 3DPR trajectory (FIG. 1). In some embodiments, the IR pulse is played out every other heartbeat, enabling interleaved dark-blood and bright-blood imaging. In certain embodiments, slab-selective excitation pulses are used to suppress the signal of epicardial fat. In certain embodiments, a respiratory navigator is used in 'monitor-only' mode with 100% gating efficiency.

In some embodiments, the scanner used in conjunction with the inventive systems and methods described herein is a 1.5T scanner. In some embodiments, the scanner is a 3T scanner. In some embodiments an MRI scanner with a magnetic field strength of 0.3-9.4T can be used in conjunction with the inventive systems and methods described herein. In some embodiments, the 3T scanner is a 3T scanner Siemens Magnetom Trio. In some embodiments, the following imaging parameters are used in conjunction with the inventive systems and methods described herein: a whole-heart 3D sagittal slab with FOV=$50^3$mm$^3$-$600^3$mm$^3$; matrix size=$64^3$-$1024^3$; spatial resolution=0.4 mm$^3$-5 mm$^3$; FA=$1°$-$90°$; TR/TE=0.5/0-40/20 ms; BW=50-2000 Hz/pixel; total projections=100-500000; scan time 0.5-60 minutes depending on heart rate.

In an embodiment, FOV=$330^3$mm$^3$; matrix size=$288^3$; spatial resolution=1.13 mm$^3$; FA=$12°$; TR/TE=4.6/2.3 ms; BW=721 Hz/pixel; total projections=8500; scan time≈10 mins depending on heart rate.

Image Reconstruction Techniques

In various embodiments, retrospective motion correction is performed with an integrated self-calibrating iterative SENSE scheme. In certain embodiments, both dark-blood and bright-blood k-space data are segmented into respiratory bins using the navigator signal as a uniform reference. In certain embodiments, both dark-blood and bright-blood k-space data are segmented into from 2-20 respiratory bins using the navigator signal as a uniform reference. In certain embodiments, both dark-blood and bright-blood k-space data are segmented into six respiratory bins using the navigator signal as a uniform reference. In some embodiments, an image-based affine motion correction algorithm is first used to correct for respiratory motion between different bins using the high signal-to-noise ratio (SNR) bright-blood data, and then shared with/applied to both dark-blood and bright-blood images. In some embodiments, the image-based affine motion correction algorithm utilized in conjunction with the inventive systems tdand methods described herein is as described in Pang J. et al, MRM; 2014:71, which is hereby incorporated herein by reference in its entirety as though fully set forth. Essentially, motion transform parameters are derived by registering each binned image onto the reference image in the image domain. The resultant transform parameters are utilized to determine the proper k-space phase shifts in order to correct the motion in each bin of MR measurement data.

In various embodiments, the invention teaches a method for performing MRI on a subject to acquire sets of images of an object within the subject in one scan, each set having a distinct contrast weighting. In some embodiments described herein and demonstrated in the ensuing examples, the object comprises, consists of, or consists essentially of one or more region of the subject's heart. In some embodiments, the object comprises, consists of, or consists essentially of the entire heart of the subject. In some embodiments, the method comprises, consists of, or consists essentially of (a) positioning the object in a magnetic field; (b) with a radio frequency (RF) coil, applying none, one, or more preparatory pre-pulses during one or more repetition period to selectively suppress the signal of one or more material/component of the object, based on different relaxation times; (c) applying readout pulses to acquire imaging data in an interleaved fashion for different sets of images during multiple repetitions; and (d) overlaying and color-coding images with different contrast weightings. In certain embodiments, step (b) includes applying one or more preparatory pulses which comprise, consist of, or consist essentially of a 180 degree inversion pulse, a T2 preparation pulse, or both a 180 degree inversion pulse and a T2 preparation pulse. In some embodiments, different relaxation times comprise, consist of, or consist essentially of spin-lattice (T1) relaxation times and spin-spin (T2) relaxation times. In some embodiments, the selectively suppressed signal of step (b) may include, but is in no way limited to that of blood, contrast-enhanced blood, adipose tissue, myocardium, normal vessel wall, fibrous plaque tissue, and the like.

In various embodiments, the invention teaches a method for signal processing to compensate for motion-induced artifacts in MR measurement data with multiple image contrasts. In some embodiments, the method comprises, consists of, or consists essentially of the steps of: (a) separating acquired imaging data into a plurality of datasets based on different image contrasts; (b) sorting each dataset into different data groups corresponding to different motion phases using a diaphragm navigator or self-navigation signal as a reference; (c) automatically selecting the dataset with the highest signal-to-noise ratio for motion estimation; (d) estimating the motion between a reference data group and the rest of the data groups using image-based 3D affine registration, as described herein; and (e) modifying each dataset and adjusting trajectory based on translation vectors and affine transform matrices to compensate for the estimated motion, as determined in step (d), thereby resulting in motion-corrected k-space data and trajectory. In some embodiments, the resulting motion-corrected k-space data and trajectory are incorporated into a conjugate gradient (CG-) sensitivity encoding (SENSE) reconstruction framework, which includes coil sensitivity self-calibration, as described herein.

In certain embodiments, the coil sensitivity self-calibration utilized in conjunction with the inventive systems and methods described herein comprises, consists of, or consists essentially of the steps of: (a) reconstructing motion-corrected individual coil images by gridding; (b) calculating coil sensitivity maps by using eigenvector of local signal covariance matrices as the estimate of the respective sensitivity values at a specific spatial location; and (c) averaging the local image covariance matrices to suppress streaking artifacts. In some embodiments, the averaging operation is implemented in MATLAB using a graphical processing unit (GPU). In certain embodiments, the sensitivity encoding operation is performed using a gridding/regridding approach with a density compensation function (DCF) iteratively calculated from the k-space trajectory to compensate for sampling non-uniformity. In some embodiments, preconditioning by density compensation is used to accelerate convergence of the CG iterations.

In various embodiments, the invention teaches a method of signal processing to adjust inversion time retrospectively after data acquisition for selecting the optimal image contrast weighting. In some embodiments, the MRI data are acquired using 3D radial trajectory with golden angle. In certain embodiments, the acquired MR data during each TR are segmented into several groups, each with a distinct inversion time. In some embodiments, the method further includes, applying a sliding window filter to combine segmented MR data with different inversion times, while preserving distinct contrast weightings. In certain embodiments, the segmented and filtered MR data are reconstructed to multi-frame images. In certain embodiments, the density compensation function for each phase is calculated from the corresponding filtered k-space data. In some embodiments, the invention further includes displaying and selecting the frame with the best available contrast weighting. In this context, the best available contrast weighting is the contrast weighting that makes the abnormality/lesion most distinguishable from the normal/background tissue.

Figure 9:
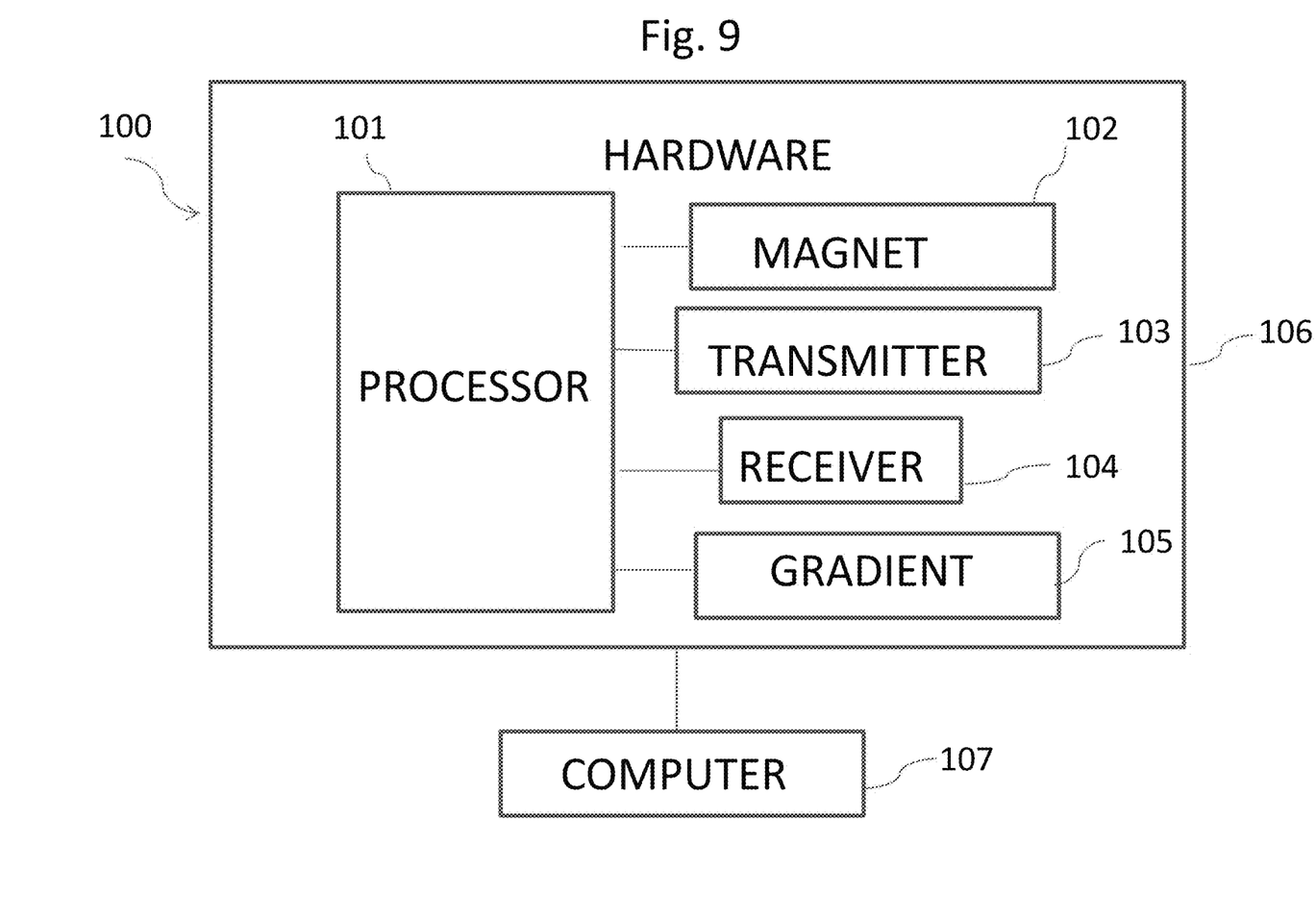
FIG. 9 depicts, in accordance with an embodiment of the invention, an MRI system that can be used in conjunction with the inventive methods.

One of skill in the art would readily appreciate that several different types of imaging systems could be used to perform the inventive methods described herein, including all of the types of imaging systems described herein, as well as similar systems. Further, by way of non-limiting example, FIG. 9 depicts a view of a system 100 that can be used to accomplish the inventive methods. System 100 includes hardware 106 and computer 107. Hardware 106 includes magnet 102, transmitter 103, receiver 104, and gradient 105, all of which are in communication with processor 101. Magnet 102 can include a permanent magnet, a superconducting magnet, or other type of magnet. Transmitter 103 along with receiver 104, are part of the RF system. Transmitter 103 can represent a radio frequency transmitter, a power amplifier, and an antenna (or coil). Receiver 104, as denoted in the figure, can represent a receiver antenna (or coil) and an amplifier. In the example shown, transmitter 103 and receiver 104 are separately represented, however, in one example, transmitter 103 and receiver 104 can share a common coil. Hardware 106 includes gradient 105. Gradient 105 can represent one or more coils used to apply a gradient for localization.

Processor 101, in communication with various elements of hardware 106, includes one or more processors configured to implement a set of instructions corresponding to any of the methods disclosed herein. Processor 101 can be configured to implement a set of instructions (stored in a memory of hardware 106) to provide RF excitation and gradients and receive magnetic resonance data from a volume of interest (VOI) comprising an object (e.g. the heart or portion of the heart of a subject).

Computer 107 is coupled to hardware 106. Computer 107 can include one or more of a desktop computer, a workstation, a server, or a laptop computer. In one example, computer 107 is user-operable and includes a display, a printer, a network interface or other hardware to enable an operator to control operation of the system 100.

In various embodiments, the invention further teaches a non-transitory machine-readable medium having machine executable instructions for causing one or more processors of a magnetic resonance imaging (MRI) machine (such as any of those described herein) to execute a method, including (1) applying the pulse sequence of any of the embodiments described herein to a VOI in a subject, and (2) applying an image reconstruction scheme described herein to reconstruct one or more images of one or more objects within the VOI. In some embodiments, the VOI comprises, consists of, or consists essentially of the subject's heart. In some embodiments, the VOI comprises, consists of, or consists essentially of a region of a subject's heart. In some embodiments, the region of the subject's heart comprises one or more blood vessels. In some embodiments, one or more of the one or more blood vessels contains plaque. In some embodiments, one or more of the one or more blood vessels contains an intra-plaque hemorrhage. In some embodiments, on or more blood vessels contains inflammation. In some embodiments, one or more of the one or more blood vessels is an artery.

In various embodiments, the invention teaches a method that comprises, consists of, or consists essentially of (1) applying the pulse sequence of any of the embodiments described herein to a VOI in a subject, and (2) applying an image reconstruction scheme described herein to reconstruct one or more images of one or more objects within the VOI. In some embodiments, the method further includes diagnosing the subject with the presence or absence of CAD on the basis of one or more images of one or more objects within the VOI. In some embodiments, the VOI comprises, consists of, or consists essentially of the subject's heart. In some embodiments, the VOI comprises, consists of, or consists essentially of a region of a subject's heart. In some embodiments, the region of the subject's heart includes one or more blood vessels. In some embodiments, one or more of the blood vessels is an artery. In some embodiments, the subject is diagnosed with CAD if one or more of the blood vessels contain plaque. In some embodiments, the subject is diagnosed with CAD if one or more of the blood vessels contain an intra-plaque hemorrhage. In some embodiments, the subject is diagnosed with CAD if one or more region of one or more blood vessels is inflamed. In some embodiments, rather than diagnosing the subject with CAD, the subject is diagnosed with one or more specific characteristic visualized (i.e. plaque, intra-plaque hemorrhage, inflammation, and the like). One skilled in the art will recognize many methods and materials similar or equivalent to those described herein, which could be used in the practice of the present invention. Indeed, the present invention is in no way limited to the methods and materials described herein or set forth in the ensuing non-limiting example.

EXAMPLES

Example 1

Figure 6:
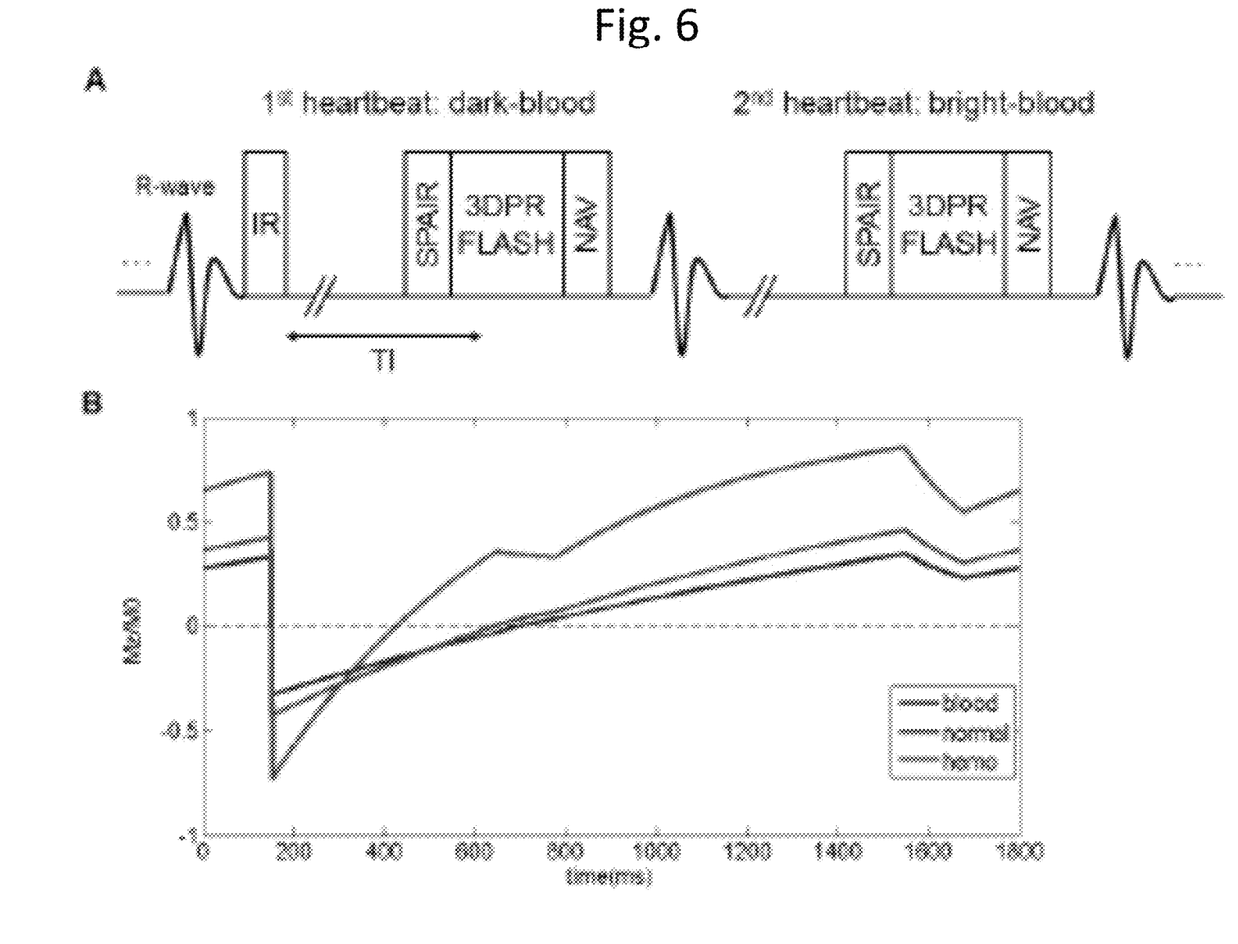
FIG. 6 depicts, in accordance with an embodiment of the invention, (A) a sequence diagram of three-dimensional projection reconstruction (3DPR) interleaved dark-blood (T1w) and bright-blood coronary imaging. (B) shows a simulated steady-state signal behavior of different tissue types.

Time-Efficient Whole-Heart Coronary Plaque Characterization with Simultaneously Acquired MRA Methods Pulse Sequence The pulse sequence consists of ECG-gated, inversion recovery (IR) prepared spoiled gradient echo (FLASH) acquisition with golden-angle 3DPR trajectory (FIG. 6). The IR pulse is played out every other heartbeat, enabling interleaved dark-blood and bright-blood imaging. Slab-selective excitation pulses are used to suppress outer-volume.

Spectral Adiabatic Inversion

Recovery (SPAIR) is used together with water-only excitation pulses to suppress the signal of epicardial fat. A respiratory navigator is used in 'monitor-only' mode with 100% gating efficiency.

Image Reconstruction

Retrospective motion correction is performed with an integrated self-calibrating iterative SENSE scheme. Both dark-blood and bright-blood k-space data are segmented into six respiratory bins using the navigator signal as a uniform reference. An image-based affine motion correction algorithm (as described herein and in Pang J. et al., MRM; 2014:71, which is hereby incorporated herein by reference in its entirety as though fully set forth) is used to correct for respiratory motion between different bins using the higher SNR bright-blood data. Identical motion transformation matrices are then shared by both dark-blood and bright-blood images.

In Vivo Imaging

Healthy volunteers (n=12) and stable CAD patients with noncalcified plaques found on CT angiography (n=11) were scanned on a 3T scanner (Siemens Magnetom Trio) pre- and post-CE (Dotarem@0.1 mmol/kg, 30 mins delay) with the following parameters: whole-heart 3D sagittal slab with FOV=$330^3$mm$^3$; matrix size=$288^3$; spatial resolution=1.13 mm$^3$; FA=12°; TR/TE=4.6/2.3 ms; BW=721 Hz/pixel; total projections=8500; scan time≈10 mins depending on heart rate. After completing MRI patients underwent interventional X-ray angiography and intracoronary optical coherence tomography (OCT) for coronary plaque evaluation.

Results

All 23 subjects successful completed the pre-CE MRI. Six eligible patients also completed the post-CE imaging. None of the healthy subjects showed hyper-intensive plaques (HIPs) whereas 2 and 3 patients showed HIPs on pre-CE and post-CE MRI, respectively.

Figure 7:
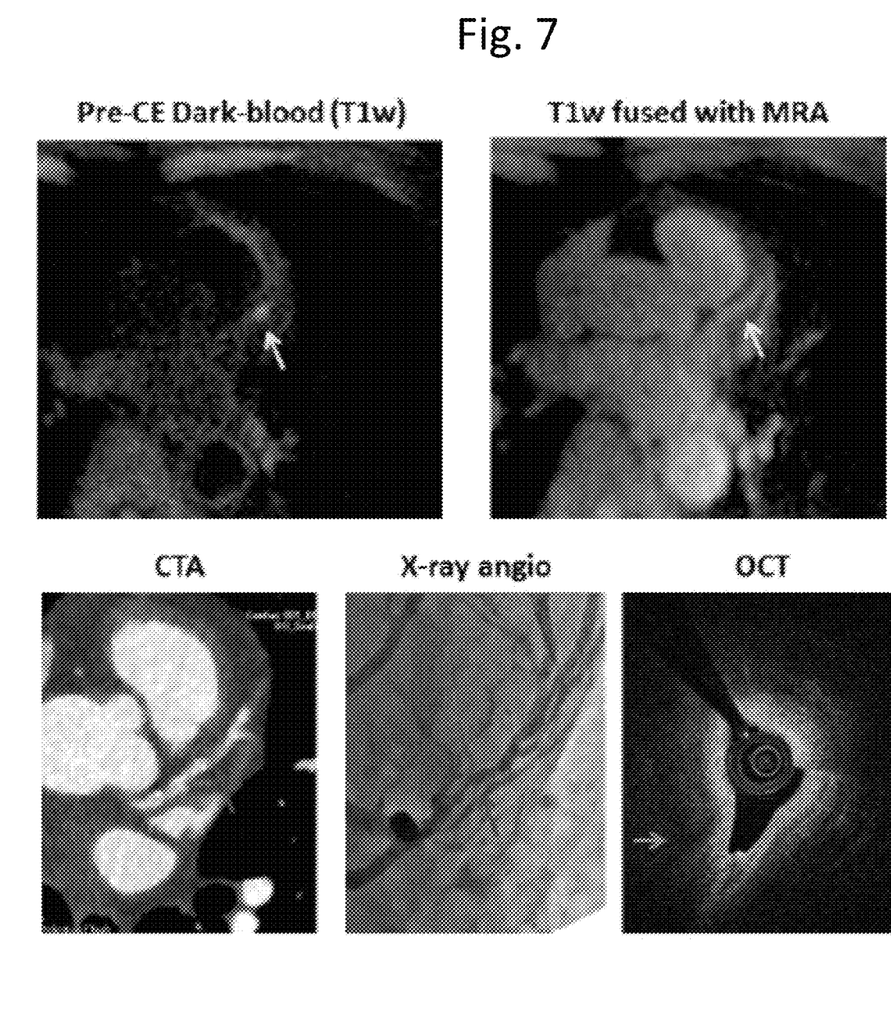
FIG. 7 depicts, in accordance with an embodiment of the invention, a CAD patient with likely intra-plaque hemorrhage.

As demonstrated in FIG. 7, a pre-CE T1W image showed a HIP localized on MRA at mid-LAD (yellow arrows). CTA and Xray showed significant stenosis and the plaque appeared to be low-density (red arrows). OCT image showed signal-poor area (blue arrow) suggestive of possible lipid core/intra-plaque hemorrhage.

Figure 8:
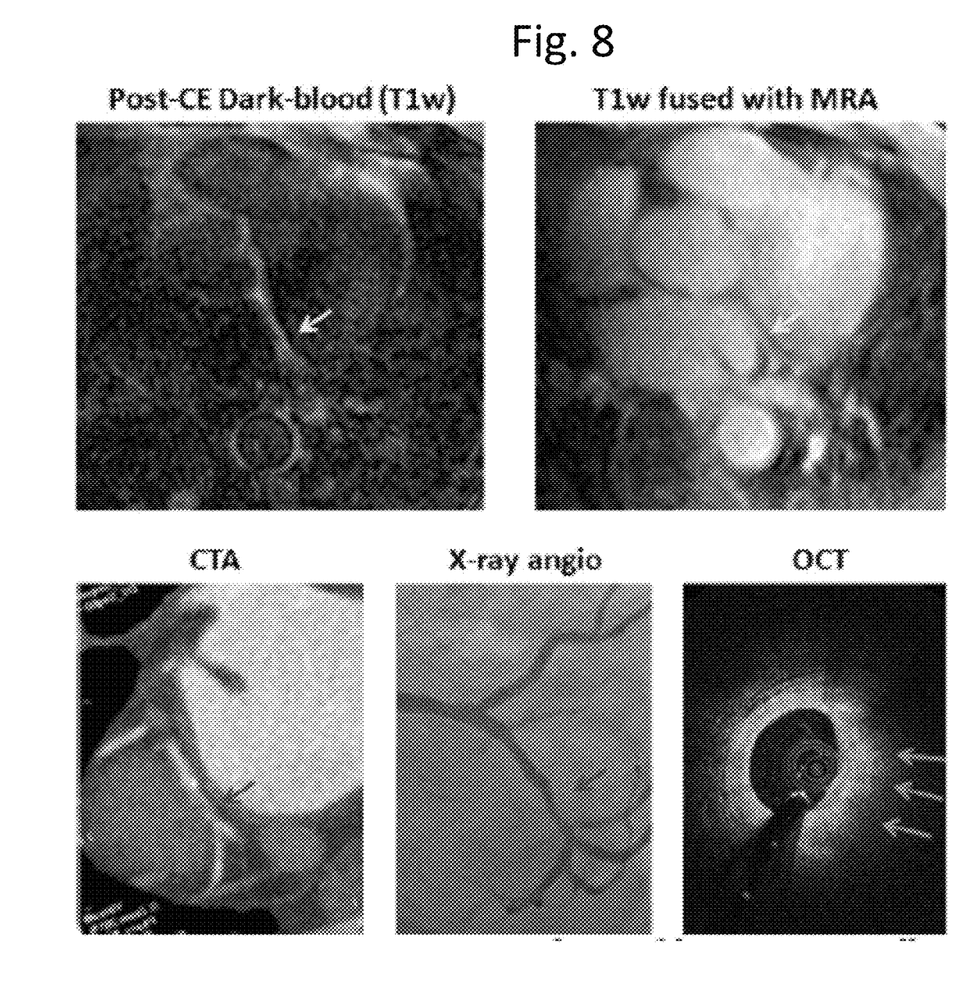
FIG. 8 depicts, in accordance with an embodiment of the invention, a CAD patient with likely coronary wall inflammation.

As demonstrated in FIG. 8, a delayed post-CE T1w image showed diffused wall enhancement localized on MRA at mid-LCX (yellow arrows). CTA and X-ray showed only moderate stenosis (red arrows). An OCT image showed strong multi-focal back reflections and signal heterogeneity within the overlying tissue suggestive of high macrophage density (blue arrows).

Discussion

The 3DPR method described above allows, for the first time, whole-heart coronary plaque characterization with simultaneously acquired bright-blood MRA. The MRA images are inherently co-registered to the T1w images therefore may be used for localizing lesions and evaluating luminal stenosis. With the help from advanced motion correction (100% respiratory gating efficiency) and parallel imaging (SENSE), isotropic high resolution coronary imaging was possible within clinically feasible scan time (10 mins). Comparison with OCT strongly suggested that the HIPs on the pre- and post-CE images may be associated with lipid core/hemorrhage and neovascularization/inflammation, respectively.

Conclusion

Time-efficient T1w whole-heart coronary plaque imaging with isotropic high resolution and simultaneously acquired MRA was feasible. The method may be able to characterize different plaque components in the coronary wall.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law.

Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for performing magnetic resonance imaging (MRI), comprising:
    positioning an object in a magnetic field;
    using a radio frequency (RF) coil to apply a plurality of preparatory pulses to the object and a plurality of readout pulses to the object,
        one of the plurality of preparatory pulses and one of the plurality of readout pulses being applied during each of a plurality of repetition periods,
        the plurality of preparatory pulses alternating between 180° inversion pulses configured to selectively suppress a signal of blood components of the object, and T2 preparation pulses configured to selectively suppress a signal of components of the object other than blood, and
        the plurality of preparatory pulses being based on a relaxation time of the blood components of the object being different than a relaxation time of the components of the object other than blood;
    acquiring, responsive to the plurality of preparatory pulses and the plurality of readout pulses, imaging data corresponding to at least a set of dark blood images of the object and a set of bright blood images of the object,
        the set of dark blood images having a first contrast weighting and being associated with the 180° inversion pulses,
        the set of bright blood images having a second contrast weighting and being associated with the T2 preparation pulses, and
        the second contrast weighting being different than the first contrast weighting; and
    overlaying and color-coding the set of dark blood images having the first contrast weighting and the set of bright blood images having the second contrast weighting.

2. The method of claim 1, wherein the relaxation time of the blood components of the object and the relaxation time of the components of the object other than blood include (i) a spin-lattice T1 relaxation time, (ii) a spin-spin T2 relaxation time, or (iii) both (i) and (ii).

3. The method of claim 1, wherein the object comprises one or more portion of a subject's heart.

4. The method of claim 1, wherein the object comprises a subject's heart.

5. The method of claim 1, further comprising:
    sorting the imaging data into a plurality of sets of imaging data, each of the plurality of sets of imaging data corresponding to a different contrast weighting;
    sorting each of the plurality of sets of imaging data into one or more data groups to thereby obtain a plurality of data groups, each of the one or more data groups for each of the plurality of sets of imaging data corresponding to different motion phases of the object;
    determining a signal-to-noise ratio of the imaging data for each of the one or more data groups;
    selecting one of the one or more data groups to use as a reference data group for motion estimation, the selected one of the one or more data groups having a highest signal-to-noise ratio among the one or more data groups;
    estimating motion represented by a difference in the motion phase of the reference data group and the motion phase of each of other data groups of the one or more data groups using image-based 3D affine registration; and
    modifying each of the plurality of sets of imaging data and adjusting trajectory of the object represented in the plurality of sets of imaging data using translation vectors and affine transform matrices to compensate for the estimated motion, thereby resulting in motion-corrected k-space data and motion-corrected trajectory.

6. The method of claim 5, wherein the motion-corrected k-space data and the motion-corrected trajectory are calibrated to adjust for a sensitivity of the RF coil.

7. The method of claim 6, wherein the calibration comprises:
    gridding the motion-corrected k-space data to thereby reconstruct motion-corrected individual coil images;
    calculating coil sensitivity maps by using an eigenvector of one or more local signal covariance matrices as an estimate of respective sensitivity values at a spatial location of the motion-corrected individual coil images; and
    averaging the one or more local signal covariance matrices to suppress streaking artifacts in the motion-corrected individual coil images.

8. The method of claim 1, wherein the acquired imaging data is segmented into a plurality of groups, each of the plurality of groups having a distinct inversion time.

9. The method of claim 8, further comprising applying a sliding window filter to combine the segmented imaging data.

10. The method of claim 9, wherein the imaging data is reconstructed into multi-frame images after being segmented and combined.

11. A non-transitory machine-readable medium having machine executable instructions for causing one or more processors of a magnetic resonance imaging (MRI) machine to execute a method, the method comprising:
    applying, using a radio frequency (RF) coil, a plurality of preparatory pulses to the object and a plurality of readout pulses to the object,
        one of the plurality of preparatory pulses and one of the plurality of readout pulses being applied during each of a plurality of repetition periods, the plurality of preparatory pulses alternating between 180° inversion pulses configured to selectively suppress a signal of blood components of the object, and T2 preparation pulses configured to selectively suppress a signal of components of the object other than blood, and the plurality of preparatory pulses being based on a relaxation time of the blood components of the object being different than a relaxation time of the components of the object other than blood;

acquiring, responsive to the plurality of preparatory pulses and the plurality of readout pulses, imaging data corresponding to at least a set of dark blood images of the object and a set of bright blood images of the object, the set of dark blood images having a first contrast weighting and being associated with the 180° inversion pulses, the set of bright blood images having a second contrast weighting and being associated with the T2 preparation pulses, and the second contrast weighting being different than the first contrast weighting; and overlaying and color-coding the set of dark blood images having the first contrast weighting and the set of bright blood images having the second contrast weighting.

12. The non-transitory machine-readable medium of claim 11, wherein the relaxation time of the blood components of the object and the relaxation time of the components of the object other than blood include (i) a spin-lattice T1 relaxation time, (ii) a spin-spin T2 relaxation time, or (iii) both (i) and (ii).

13. The non-transitory machine-readable medium of claim 11, wherein the MRI machine is a 3.0 Tesla machine.

14. The non-transitory machine-readable medium of claim 11, wherein the object comprises one or more portion of a subject's heart.

15. The non-transitory machine-readable medium of claim 11, wherein the object comprises a subject's heart.

* * * * *

UNITED STATES PATENT AND TRADEMARK OFFICE
CERTIFICATE OF CORRECTION

PATENT NO. : 10,634,752 B2
APPLICATION NO. : 14/853091
DATED : April 28, 2020
INVENTOR(S) : Li et al.

It is certified that error appears in the above-identified patent and that said Letters Patent is hereby corrected as shown below:

In the Specification

In Column 1, under the title of the invention, insert the following paragraph at Line 5:
--STATEMENT REGARDING FEDERALLY SPONSORED RESEARCH AND DEVELOPMENT
This invention was made with government support under Grant No. EB002623, awarded by the National Institutes of Health. The Government has certain rights in the invention.--

Signed and Sealed this
Tenth Day of September, 2024

Katherine Kelly Vidal
*Director of the United States Patent and Trademark Office*